(12) United States Patent
Mamandipoor et al.

(10) Patent No.: US 12,390,119 B2
(45) Date of Patent: Aug. 19, 2025

(54) SYSTEMS AND METHODS FOR RADAR-BASED BIOMETRIC SIGNAL EXTRACTION

(71) Applicant: Apple Inc., Cupertino, CA (US)

(72) Inventors: Babak Mamandipoor, San Jose, CA (US); James T Curran, Cupertino, CA (US); Joseph Hakim, Soquel, CA (US)

(73) Assignee: Apple Inc., Cupertino, CA (US)

( * ) Notice: Subject to any disclaimer, the term of this patent is extended or adjusted under 35 U.S.C. 154(b) by 300 days.

(21) Appl. No.: 17/880,306

(22) Filed: Aug. 3, 2022

(65) Prior Publication Data

US 2023/0092386 A1 Mar. 23, 2023

Related U.S. Application Data

(60) Provisional application No. 63/247,130, filed on Sep. 22, 2021.

(51) Int. Cl.
*A61B 5/05* (2021.01)
*A61B 5/0205* (2006.01)
*A61B 5/024* (2006.01)
*A61B 5/08* (2006.01)

(52) U.S. Cl.
CPC .............. *A61B 5/05* (2013.01); *A61B 5/0205* (2013.01); *A61B 5/02444* (2013.01); *A61B 5/0816* (2013.01)

(58) Field of Classification Search
CPC ....................................................... A61B 5/05
See application file for complete search history.

(56) References Cited

U.S. PATENT DOCUMENTS

| | | | |
|---|---|---|---|
| 8,026,840 | B2 | 9/2011 | Dwelly et al. |
| 8,884,813 | B2 | 11/2014 | Bangera et al. |
| 9,549,691 | B2 | 1/2017 | Tran |
| 10,201,278 | B2 | 2/2019 | Lux et al. |
| 10,401,479 | B2 | 9/2019 | Mabrouk et al. |
| 10,642,367 | B2 | 5/2020 | Poupyrev |

(Continued)

FOREIGN PATENT DOCUMENTS

EP 3492945 A1 6/2019

OTHER PUBLICATIONS

Alizadeh Mostofaf et al.: "Remote Monitoring of Human Vital Signs Using mm-Wave FMCW Radar"; IEEE Access, vol. 7, Apr. 23, 2019; pp. 54958-54968; (XP011723382).

(Continued)

*Primary Examiner* — Joel F Brutus
(74) *Attorney, Agent, or Firm* — FLETCHER YODER PC

(57) ABSTRACT

Systems and methods for determining fine grain motions and vibrations of live and/or inanimate objects are described based on using a radar system. For example, biometric information may be extracted from such vibrations associated with a live object. In different embodiments, processing circuitry may perform different statistical analysis on reflections from the objects. Moreover, the processing circuitry may perform different processing functions based on the statistical analysis to determine the vibrations with high accuracy. Furthermore, the processing circuitry may also select one or multiple target maps based on a field of view of the radar system for a more robust measurement of the vibrations associated with one or multiple objects.

20 Claims, 11 Drawing Sheets

(56) References Cited

U.S. PATENT DOCUMENTS

| | | |
|---|---|---|
| 11,170,899 B2 | 11/2021 | Choi et al. |
| 2012/0245479 A1 | 9/2012 | Ganesh et al. |
| 2013/0030257 A1 | 1/2013 | Nakata et al. |
| 2018/0279884 A1* | 10/2018 | Ahmad .................. G01S 13/88 |
| 2021/0255302 A1 | 8/2021 | Liu et al. |

OTHER PUBLICATIONS

Extended European Search Report for European Patent Application No. 22190778.5 dated Feb. 13, 2023; 14 pgs.

* cited by examiner

SYSTEMS AND METHODS FOR RADAR-BASED BIOMETRIC SIGNAL EXTRACTION

CROSS-REFERENCE TO RELATED APPLICATION

This application claims priority to U.S. Provisional Application No. 63/247,130, filed Sep. 22, 2021, entitled "SYSTEMS AND METHODS FOR RADAR-BASED BIOMETRIC SIGNAL EXTRACTION," the disclosure of which is incorporated by reference herein in its entirety for all purposes.

BACKGROUND

The present disclosure relates generally to biometric information, and more specifically to determining biometric information using radar-based systems.

An electronic device may include a radar system having a transmitter and a receiver. The transmitter may transmit a signal to a target object and the receiver may receive a reflection of the transmitted signal from the target object. As such, the radar system may detect a movement or vibration of the target object based on the reflected signal. However, in some cases, the reflection of the transmitted signal may be ambiguous, discontinuous, experience interference, or may otherwise be interpreted by the electronic device with error. Moreover, these erroneous behavior may be amplified when detecting smaller movements or vibrations, such as breathing and/or heart rate of a live object.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, an electronic device is described. The electronic device may include a transmitter that may transmit a plurality of signals toward a live target. The electronic device may also include a receiver that may receive reflections of the plurality of signals reflected from the live target. Moreover, the electronic device may include one or more processors that may receive the reflections from the receiver, determine a set of differential phases of a subplurality of the reflections, determine a normality set of differential phases based on performing a statistical analysis on the set of differential phases, and generate biometric time-series data based on the normality set of differential phases.

In another embodiment, a method of operating an electronic device is described. The method may include receiving multiple signals back-scattered from a live target, generating multiple target maps, each target map including a subplurality of signals of the multiple signals based on a distance range, azimuth range, elevation range, doppler dimensions range, or any combination thereof, receiving multiple biometric time-series data associated with the live target for each of the multiple target maps and fusing the multiple biometric time-series data to determine an output biometric time-series data associated with the live target.

In yet another embodiment, one or more tangible, non-transitory, computer-readable media comprising instructions is described. The instructions, when executed by one or more processors, may cause the one or more processors to receive multiple signals back-scattered from a live target, generate multiple target maps, each target map including a subplurality of signals of the multiple signals based on a distance range, azimuth range, elevation range, doppler dimensions range, or any combination thereof, receive multiple biometric time-series data associated with the live target for each of the multiple target maps and fuse the multiple biometric time-series data to determine an output biometric time-series data associated with the live target.

Various refinements of the features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings described below in which like numerals refer to like parts.

DETAILED DESCRIPTION OF SPECIFIC EMBODIMENTS

Figure 1:
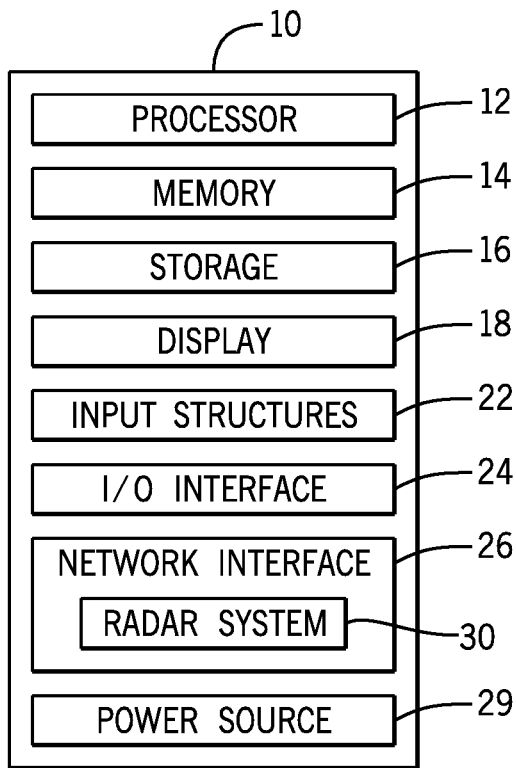
FIG. 1 is a block diagram of an electronic device, according to embodiments of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

Furthermore, the particular features, structures, or characteristics may be combined in any suitable manner in one or more embodiments. Use of the terms "approximately," "near," "about," "close to," and/or "substantially" should be understood to mean including close to a target (e.g., design, value, amount), such as within a margin of any suitable or contemplatable error (e.g., within 0.1% of a target, within 1% of a target, within 5% of a target, within 10% of a target, within 25% of a target, and so on). Moreover, it should be understood that any exact values, numbers, measurements, and so on, provided herein, are contemplated to include approximations (e.g., within a margin of suitable or contemplatable error) of the exact values, numbers, measurements, and so on.

A live object, such as a human body, may generate fine grain motions or vibrations. For example, a respiratory and/or cardiovascular function of a human body may induce the fine grain motions or vibrations on human skin. "Fine grain" motions or vibrations may refer to small displacement motions or vibrations on the order of a few millimeters (mm) or a few centimeters (cm) (e.g., 0.5 mm or less, 1 mm or less, 2 mm or less, 5 mm or less, 1 cm or less, 2 cm or less, 5 cm or less, and so on). For example, the fine grain motions or vibrations may include movements such as those associated with a rate of breathing, a rate of heartbeat, coughing, sneezing, tremors, seizures, and/or other movements or vibrations of the human body, or any combination of the above.

An electronic device may detect such vibrations of the human body using the systems and methods described herein. For example, the electronic device may include a radar system including a transmitter and a receiver. In some cases, the transmitter may couple to one or more transmitter antennas and the receiver may couple to one or more receiver antennas. However, in alternative or additional embodiments, the transmitter and the receiver may share one or more antennas of the electronic device.

In any case, the transmitter may transmit one or more signals to the human body and the receiver may receive one or more reflections of the signals (or back-scattered signals) reflected from the human body. For example, the transmitter may transmit one or more chirp signals, with increasing or decreasing frequency over a frequency range, and the receiver may receive reflections of the one or more chirp signals. Subsequently, the electronic device may determine differential phases (e.g., phase rotations between phase values of consecutive reflections) and/or frequency changes (e.g., frequency modulations) of the back-scattered signals caused by the vibrations of the human body. For example, the electronic device may combine and/or compare one or more of the back-scattered signals with corresponding instances of the one or more transmitted signals to determine the differential phases and/or the frequency modulations of the back-scattered signals caused by the vibrations of the human body. The differential phases may include a change in phase (e.g., phase value) of reflections received in different time epochs (e.g., consecutively). Such time epochs may correspond to consecutive received reflections, consecutive time windows, consecutive chirp signals, or any other viable time epochs for determining the differential phases.

Moreover, the electronic device may transmit and receive the signals consecutively to determine the vibrations of the human body over a period of time. For example, the electronic device may determine biometric information, such as the respiratory and/or cardiovascular function of the human body, based on determining the differential phases and/or the frequency modulations of consecutive back-scattered signals. That said, in some embodiments, the electronic device may also determine a statistical analysis of the differential phases and/or the frequency modulations to determine the biometric information, as will be appreciated.

In some embodiments, the electronic device may determine the statistical analysis by determining (e.g., calculating) a mode, a mean, a variance, or another statistical parameter of the differential phases and/or the differential frequencies. In some cases, the statistical analysis may include determining a combination of a number of such statistical parameters. In any case, the electronic device may determine the biometric information of the human body with higher accuracy and lower error rate based on the statistical analysis of the differential phases and/or the differential frequencies. For example, in some cases, the electronic device may determine normality data by excluding outlier data. The electronic device may determine the normality data based on determining that the differential phases and/or the differential frequencies do not exceed a threshold differential phase. Moreover, the electronic device may determine the threshold p differential phase based on the statistical analysis of the differential phase and/or the differential frequencies.

In some embodiments, the electronic device may perform the statistical analysis on a subset of the back-scattered signals (e.g., on a target map of the subset of the back-scattered signals) to determine the biometric information of the human body. In some cases, the electronic device may determine the subset of the back-scattered signals based on a spatial dimension range, a range of distance(s) from the electronic device, an angular resolution range, and/or other parameters or combination of parameters associated with the live object (e.g., the human body). Alternatively or additionally, such parameters may be selected to distinguish between multiple live objects. For example, a first subset of the back-scattered signals may correspond to a first live object of multiple live objects in a field of view of the electronic device, and a second subset of the back-scattered signals may correspond to a second subset of the back-scattered signals may correspond to one of multiple live objects in a field of view of the electronic device of the multiple live objects.

In additional or alternative embodiments, the electronic device may also perform the statistical analysis on multiple subsets of the back-scattered signals. The electronic device may select multiple subsets of the back-scattered signals (e.g., generating multiple target maps) for determining the biometric information of the human body. Moreover, the electronic device may determine the multiple subsets of the back-scattered signals based on respective spatial dimension ranges, ranges of distance from the electronic device, angular resolution ranges, other parameters associated with the live object (e.g., the human body), or any combination of the above. For example, the electronic device may perform the statistical analysis on the multiple subsets in parallel, in a consecutive order, or in any other viable order.

With the foregoing in mind, in some cases, the electronic device may fuse a number of the multiple subsets of the back-scattered signals to determine the biometric information of the human body. Additionally or alternatively, the electronic device may select one or a number of the multiple subsets of the back-scattered signals for determining the biometric information of the human body. For example, the electronic device may select the one or the number of the multiple subsets based on having more reliable back-scattered signals and/or lower deviated data from a statistical parameter (e.g., mode, mean, variance) of the differential phases and/or the differential frequencies. Moreover, in yet additional or alternative cases, the electronic device may determine biometric information of different live objects (e.g., multiple humans) based on using multiple subsets of the back-scattered signals.

As such, the electronic device may provide more robust biometric information of the human body based on performing the statistical analysis. In some cases, the electronic device may reduce a phase wrapping effect based on a change in the distance of the human body from the electronic device by excluding outlier data (e.g., one or multiple data with wrapped phase) using the statistical analysis. Additionally or alternatively, performing the statistical analysis may reduce an effect of destructive or constructive interference of multiple back-scattered signals (e.g., multipath fading, clutter/interference phase reference translation problem, etc.), among other possible errors.

Accordingly, based on performing the statistical analysis, the electronic device may determine a more robust measurement of the biometric information, such as the respiratory and/or cardiovascular information of one or multiple human bodies. Moreover, in different embodiments, the biometric information may include a rate of breathing, a rate of heartbeat, coughing, sneezing, tremors, seizures, other movements or vibrations of the human body, or a combination of any of these. For example, the electronic device may output one or multiple signals including one or multiple of the above mentioned biometric information.

With the foregoing in mind, FIG. 1 is a block diagram of an electronic device 10, according to embodiments of the present disclosure. The electronic device 10 may include, among other things, one or more processors 12 (collectively referred to herein as a single processor for convenience, which may be implemented in any suitable form of processing circuitry), memory 14, nonvolatile storage 16, a display 18, input structures 22, an input/output (I/O) interface 24, a network interface 26, and a power source 29. The various functional blocks shown in FIG. 1 may include hardware elements (including circuitry), software elements (including machine-executable instructions), or a combination of both hardware and software elements (which may be referred to as logic). The processor 12, memory 14, the nonvolatile storage 16, the display 18, the input structures 22, the input/output (I/O) interface 24, the network interface 26, and/or the power source 29 may each be communicatively coupled directly or indirectly (e.g., through or via another component, a communication bus, a network) to one another to transmit and/or receive data between one another. It should be noted that FIG. 1 is merely one example of a particular implementation and is intended to illustrate the types of components that may be present in electronic device 10. For example, in some cases, the electronic device 10 may not include the display 18.

By way of example, the electronic device 10 may include any suitable computing device, including a desktop or notebook computer (e.g., in the form of a MacBook®, MacBook® Pro, MacBook Air®, iMac®, Mac® mini, or Mac Pro® available from Apple Inc. of Cupertino, California), a portable electronic or handheld electronic device such as a wireless electronic device or smartphone (e.g., in the form of a model of an iPhone® available from Apple Inc. of Cupertino, California), a tablet (e.g., in the form of a model of an iPad® available from Apple Inc. of Cupertino, California), a wearable electronic device (e.g., in the form of an Apple Watch® or HomePod® by Apple Inc. of Cupertino, California), and other similar devices. It should be noted that the processor 12 and other related items in FIG. 1 may be generally referred to herein as "data processing circuitry."

Such data processing circuitry may be embodied wholly or in part as software, hardware, or both. Furthermore, the processor 12 and other related items in FIG. 1 may be a single contained processing module or may be incorporated wholly or partially within any of the other elements within the electronic device 10. The processor 12 may be implemented with any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable entities that may perform calculations or other manipulations of information. The processors 12 may include one or more application processors, one or more baseband processors, or both, and perform the various functions described herein.

In the electronic device 10 of FIG. 1, the processor 12 may be operably coupled with a memory 14 and a nonvolatile storage 16 to perform various algorithms. Such programs or instructions executed by the processor 12 may be stored in any suitable article of manufacture that includes one or more tangible, computer-readable media. The tangible, computer-readable media may include the memory 14 and/or the nonvolatile storage 16, individually or collectively, to store the instructions or routines. The memory 14 and the nonvolatile storage 16 may include any suitable articles of manufacture for storing data and executable instructions, such as random-access memory, read-only memory, rewritable flash memory, hard drives, and optical discs. In addition, programs (e.g., an operating system) encoded on such a computer program product may also include instructions that may be executed by the processor 12 to enable the electronic device 10 to provide various functionalities.

In certain embodiments, the display 18 may facilitate users to view images generated on the electronic device 10. In some embodiments, the display 18 may include a touch screen, which may facilitate user interaction with a user interface of the electronic device 10. Furthermore, it should be appreciated that, in some embodiments, the display 18 may include one or more liquid crystal displays (LCDs), light-emitting diode (LED) displays, organic light-emitting diode (OLED) displays, active-matrix organic light-emitting diode (AMOLED) displays, or some combination of these and/or other display technologies.

The input structures 22 of the electronic device 10 may enable a user to interact with the electronic device 10 (e.g., pressing a button to increase or decrease a volume level). The I/O interface 24 may enable electronic device 10 to interface with various other electronic devices, as may the network interface 26. In some embodiments, the I/O interface 24 may include an I/O port for a hardwired connection for charging and/or content manipulation using a standard connector and protocol, such as the Lightning connector provided by Apple Inc. of Cupertino, California, a universal serial bus (USB), or other similar connector and protocol. The network interface 26 may include, for example, one or more interfaces for a personal area network (PAN), such as an ultra-wideband (UWB) or a BLUETOOTH® network, for a local area network (LAN) or wireless local area network (WLAN), such as a network employing one of the IEEE 802.11x family of protocols (e.g., WI-FI®), and/or for a wide area network (WAN), such as any standards related to the Third Generation Partnership Project (3GPP), including, for example, a $3^{rd}$ generation (3G) cellular network, universal mobile telecommunication system (UMTS), $4^{th}$ generation (4G) cellular network, long term evolution (LTE®) cellular network, long term evolution license assisted access (LTE-LAA) cellular network, $5^{th}$ generation (5G) cellular network, and/or New Radio (NR) cellular network, a satellite network, and so on.

In particular, the network interface 26 may include, for example, one or more interfaces for using a Release-15 cellular communication standard of the 5G specifications that include the millimeter wave (mmWave) frequency range (e.g., 24.25-300 gigahertz (GHz)) and/or any other cellular communication standard release (e.g., Release-16, Release-17, any future releases) that define and/or enable frequency ranges used for wireless communication. The network interface 26 of the electronic device 10 may allow communication over the aforementioned networks (e.g., 5G, Wi-Fi, LTE-LAA, and so forth). The network interface 26 may also include one or more interfaces for, for example, broadband fixed wireless access networks (e.g., WIMAX®), mobile broadband Wireless networks (mobile WIMAX®), asynchronous digital subscriber lines (e.g., ADSL, VDSL), digital video broadcasting-terrestrial (DVB-T®) network and its extension DVB Handheld (DVB-H®) network, ultra-wideband (UWB) network, alternating current (AC) power lines, and so forth.

As illustrated, the network interface 26 may include a radar system 30. In some embodiments, all or portions of the radar system 30 may be disposed within the processor 12. The radar system 30 may support transmission and receipt of various wireless signals via one or more antennas, and thus may include a transmitter and a receiver (e.g., combined in a transceiver). In any case, the radar system 30 may transmit one or more signals and receive reflections of the one or more signals. Moreover, the radar system 30 may provide the reflections of the one or more signals to the processor 12 for determining the biometric information associated with a live object. For example, the processor 12 may use the memory 14 and/or the storage 16 to retrieve instructions, store data, and/or manipulate data to perform statistical analysis on the reflections of the one or more signals and determine the biometric information. Moreover, the processor 12 may use the display 18, the I/O interface 24, and/or any other components of the electronic device 10 to provide (e.g., output) the biometric information.

Figure 2:
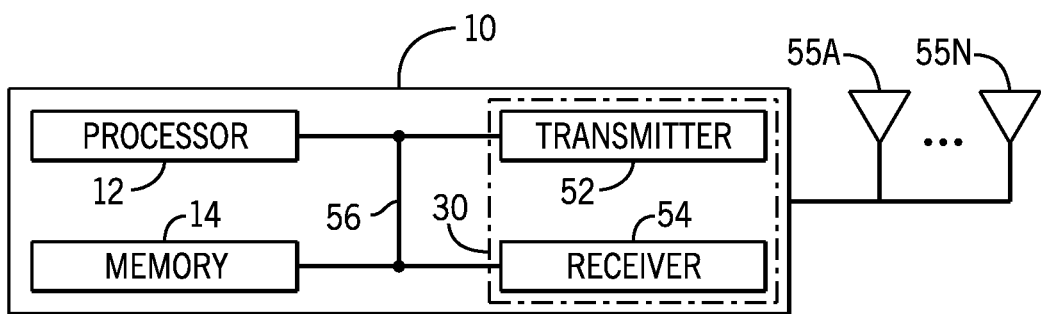
FIG. 2 is a functional diagram of the electronic device of FIG. 1, according to embodiments of the present disclosure.

FIG. 2 is a functional diagram of the electronic device 10 of FIG. 1, according to embodiments of the present disclosure. As illustrated, the processor 12, the memory 14, the radar system 30, a transmitter 52, a receiver 54, and/or antennas 55 (illustrated as 55A-55N, collectively referred to as an antenna 55) may be communicatively coupled directly or indirectly (e.g., through or via another component, a communication bus, a network) to one another to transmit and/or receive data between one another.

The electronic device 10 may include the transmitter 52 and/or the receiver 54 that respectively enable transmission and reception of data between the electronic device 10 and an external device via, for example, a network (e.g., including base stations) or a direct connection. In some cases, the transmitter 52 may transmit one or more signals at a live object. Moreover, the receiver 54 may receive reflections of the one or more signals back-scattered from the live object (e.g., also referred to as reflected or back-scattered signals). As illustrated, the transmitter 52 and the receiver 54 may be combined into the radar system 30.

The electronic device 10 may also have one or more antennas 55A-55N electrically coupled to the radar system 30. The antennas 55A-55N may be configured in an omni-directional or directional configuration, in a single-beam, dual-beam, or multi-beam arrangement, and so on. Each of the antennas 55A-55N may be associated with a one or more beams and various configurations. In some embodiments, multiple antennas of the antennas 55A-55N of an antenna group or module may be communicatively coupled to the radar system 30 and each emit radio frequency signals that may constructively and/or destructively combine to form a beam.

Moreover, the electronic device 10 may form a beam for transmitting one or more signals. For example, the transmitter 52 may transmit a signal using one or more antennas 55 to form a beam and the receiver 54 may use one or more antennas 55 (same antennas or different antennas) to receive the reflection of the signal. That said, the electronic device 10 may include multiple transmitters, multiple receivers, multiple transceivers, and/or multiple antennas as suitable for various communication standards. In some embodiments, the transmitter 52 and the receiver 54 may transmit and receive signals via other wired or wireline systems or means.

As illustrated, the various components of the electronic device 10 may be coupled together by a bus system 56. The bus system 56 may include a data bus, for example, as well as a power bus, a control signal bus, and a status signal bus, in addition to the data bus. The components of the electronic device 10 may be coupled together or accept or provide inputs to each other using some other mechanism. As mentioned above, the radar system 30 of the electronic device 10 may include the transmitter 52 and the receiver 54 that are coupled to at least one antenna to enable the electronic device 10 to transmit and receive wireless signals.

Figure 3:
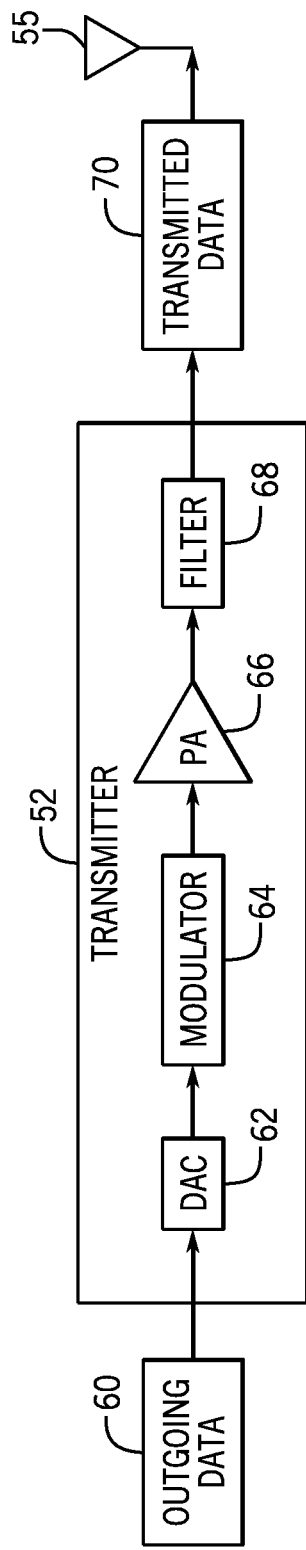
FIG. 3 is a schematic diagram of a transmitter of a radar system of the electronic device of FIG. 1, according to embodiments of the present disclosure.

FIG. 3 is a schematic diagram of the transmitter 52 (e.g., transmit circuitry) of the radar system 30, according to embodiments of the present disclosure. As illustrated, the transmitter 52 may receive outgoing signal 60 in the form of a digital signal to be transmitted via the antenna 55. In some cases, the outgoing signal 60 may include a waveform. For example, the waveform may have a specific oscillation frequency or may include a chirp signal with increasing or decreasing frequency. Moreover, in alternative or additional embodiments, the radar system 30 may use alternative or additional types of waveform such as pulse waveform, stepped-frequency continuous wave (SFCW), orthogonal frequency division multiplexing symbols (OFDM), ultra-wideband (UWB), signals of opportunity (e.g., WiFi), and/or other waveforms.

A digital-to-analog converter (DAC) 62 of the transmitter 52 may convert the digital signal to an analog signal, and a modulator 64 may combine the converted analog signal with a carrier signal to generate a radio wave. As mentioned above, such radio wave may have a specific oscillation frequency or may be a chirp signal with increasing or decreasing frequency. A power amplifier (PA) 66 may receive the modulated signal from the modulator 64. The power amplifier 66 may amplify the modulated signal to a suitable level to drive transmission of the signal via the antenna 55.

A filter 68 (e.g., filter circuitry and/or software) of the transmitter 52 may then remove undesirable noise from the amplified signal to generate transmitted signal 70 to be transmitted via the antenna 55. The filter 68 may include any suitable filter or filters to remove the undesirable noise from the amplified signal, such as a bandpass filter, a bandstop filter, a low pass filter, a high pass filter, and/or a decimation filter. Additionally, the transmitter 52 may include any suitable additional components not shown, or may not include certain of the illustrated components, such that the transmitter 52 may transmit the outgoing signal 60 via the antenna 55. For example, the transmitter 52 may include a mixer and/or a digital up converter. As another example, the transmitter 52 may not include the filter 68 if the power amplifier 66 outputs the amplified signal in or approximately in a desired frequency range (such that filtering of the amplified signal may be unnecessary).

Figure 4:
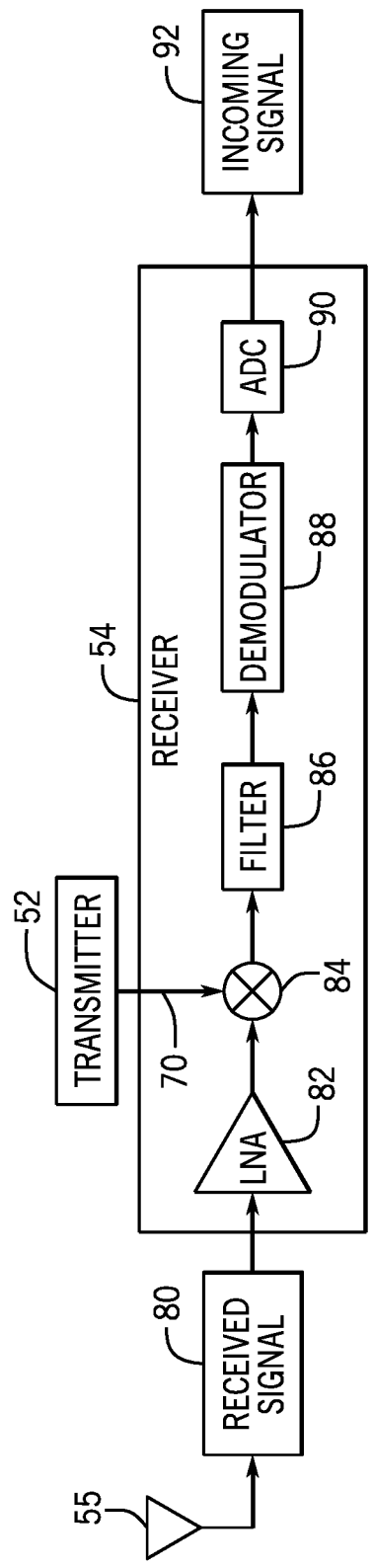
FIG. 4 is a schematic diagram of a receiver of the radar system of the electronic device of FIG. 1, according to embodiments of the present disclosure.

FIG. 4 is a schematic diagram of the receiver 54 (e.g., receive circuitry) of the radar system 30, according to embodiments of the present disclosure. As illustrated, the receiver 54 may receive received signals 80 from the antenna 55 in the form of analog signals. For example, the received signals 80 may be reflections of the transmitted signals 70 from a live object (e.g., a human body). Accordingly, the received signals 80 may have a rotated phase and/or modulated frequency caused by fine grain motions and/or vibrations of the live object.

In any case, a low noise amplifier (LNA) 82 may amplify the received analog signals to a suitable level for the receiver 54 to process. In some embodiments, a radio frequency (RF) mixer 84 may combine the output of the LNA 82 with an instance of the transmitted signals 70. For example, the transmitter 52 may provide an instance or copy of the transmitted signals 70 to the RF mixer 84. The RF mixer 84 may combine the received signals 80, provided by the LNA, and the transmitted signals 70 to determine differential phases and/or frequency modulations of the received signals 80, as will be appreciated. That said, in different embodiments, the transmitter 52 may provide an instance of the outgoing signals 60 output from the DAC 62, the modulator 64, the PA 66, or the filter 68.

A filter 86 (e.g., filter circuitry and/or software) may remove undesired noise from the received signals, such as cross-channel interference. The filter 86 may also remove additional signals received by the antenna 55 that are at frequencies other than the desired signals. The filter 86 may include any suitable filter or filters to remove the undesired noise or signals from the received signals, such as a bandpass filter, a bandstop filter, a low pass filter, a high pass filter, and/or a decimation filter.

A demodulator 88 may remove a radio frequency envelope and/or extract demodulated signals from the filtered signals for processing. An analog-to-digital converter (ADC) 90 may receive the demodulated analog signals and convert the signals to a digital signals of incoming signals 92 to be further processed by the electronic device 10. Additionally, the receiver 54 may include any suitable additional components not shown, or may not include certain of the illustrated components, such that the receiver 54 may receive the received signals 80 via the antenna 55.

Figure 5:
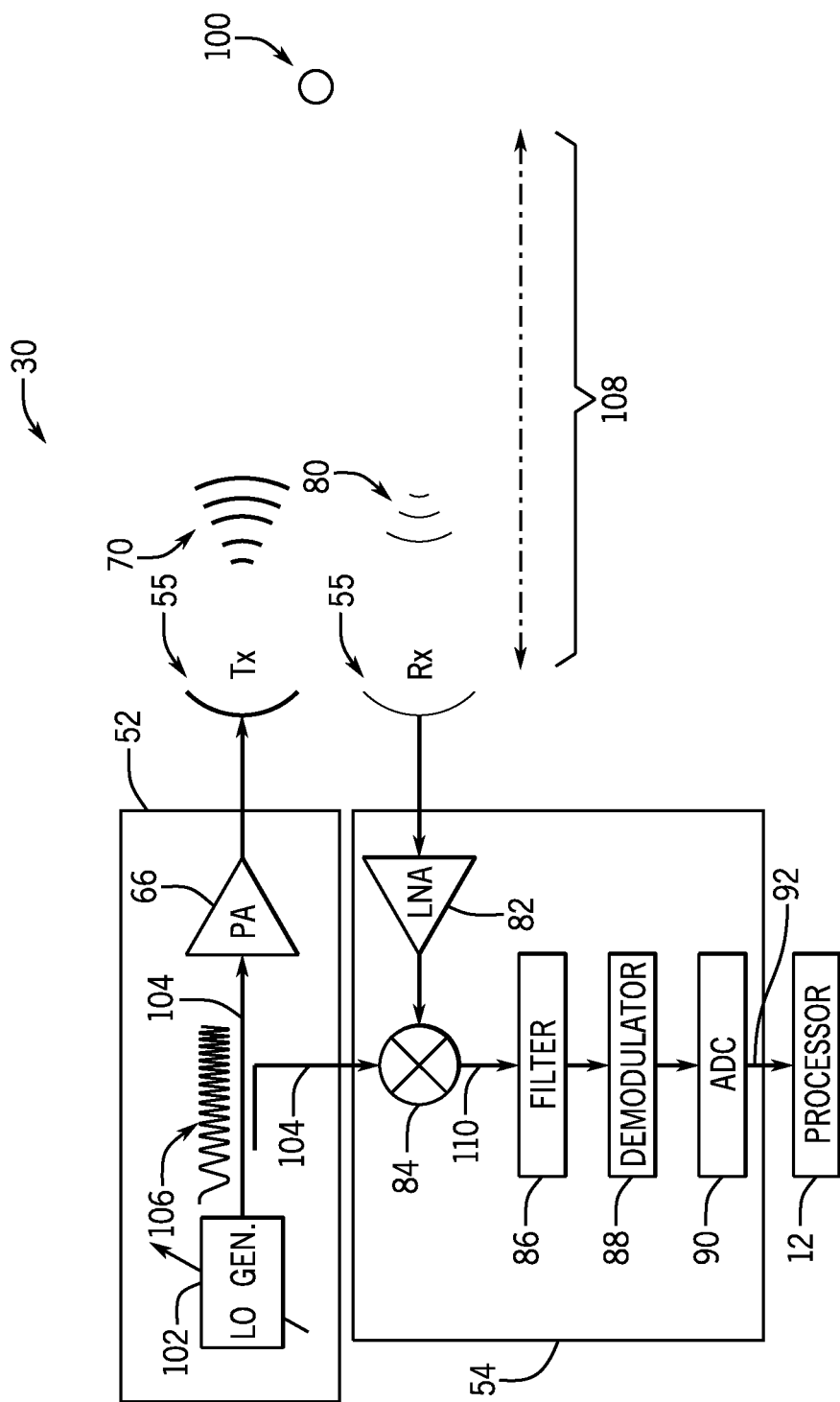
FIG. 5 is a diagram of the radar system of the electronic device of FIG. 1 transmitting signals to and receiving reflections from a point target, according to embodiments of the present disclosure.

FIG. 5 depicts the radar system 30 transmitting the transmitted signals 70 to a point target 100 and receiving the received signals 80 reflected from the point target 100. In the depicted embodiment, the transmitter 52 may include a local oscillator (LO) generator 102. The LO generator 102 may provide analog signals (e.g., including signal 104) to the PA 66. In some cases, the signal 104 may be a chirp signal 106 with increasing or decreasing frequency. However, in other cases, the signal 104 may oscillate at a specified frequency.

In any case, the PA 66 may amplify the signal 104 and send the transmitted signal 70 via the antenna 55. The point target 100 may reflect the transmitted signal 70 to the receiver 54. That is, the received signal 80 may be a reflection of the transmitted signal 70 back-scattered from the point target 100. However, fine grain motions or vibrations of the point target 100 may cause a rotation of a phase and/or a modulation in the frequency of the transmitted signal 70. For example, the point target 100 may be a part of a human body within a field of view of the radar system 30 and the vibrations may correspond to respiratory and/or cardiovascular functions of the human body. Accordingly, the received signal 80 may have a rotated phase and/or modulated frequency compared to the transmitted signal 70.

In any case, the receiver 54 may receive the received signal 80 after a roundtrip time delay (τ). In some embodiments, the processor 12 may determine the roundtrip time delay (τ). The roundtrip time delay (τ) may be related to a distance ($R_0$) 108 from the radar system 30 to the point target 100 based on Equation 1 below, where the speed of light (c) is a constant value.

$$R_0 = \frac{c\tau}{2} \quad \text{(Equation 1)}$$

Moreover, the LNA 82 may amplify the received signal 80 to a suitable level. Subsequently, the RF mixer 84 may combine the received signal 80 and an instance of the transmitted signal 70 to provide a combined signal 110. In some embodiments, the RF mixer 84 may superimpose the received signal 80 and the instance of the transmitted signal 70 to combine the signals coherently or non-coherently. For example, the RF mixer 84 may superimpose the received signal 80 and a time-shifted instance of the transmitted signal 70 to non-coherently combine the signals.

In some cases, the received signal 80 and the instance of the transmitted signal 70 may be time-synchronized. Moreover, the receiver 54 may receive multiple received signals 80 across consecutive time epochs to determine the differential phases of the received signals 80 between the consecutive time epochs. Accordingly, the processor 12 may determine a differential phase and/or frequency modulation of the received signal 80 using the combined signal 110. As discussed above, in some cases, the receiver 54 may use the filter 86, the demodulator 88, and/or the ADC 90, and provide the incoming signal 92 to the processor 12. The processor 12 may determine the differential phase and/or frequency modulation using the incoming signal 92.

Figure 6:
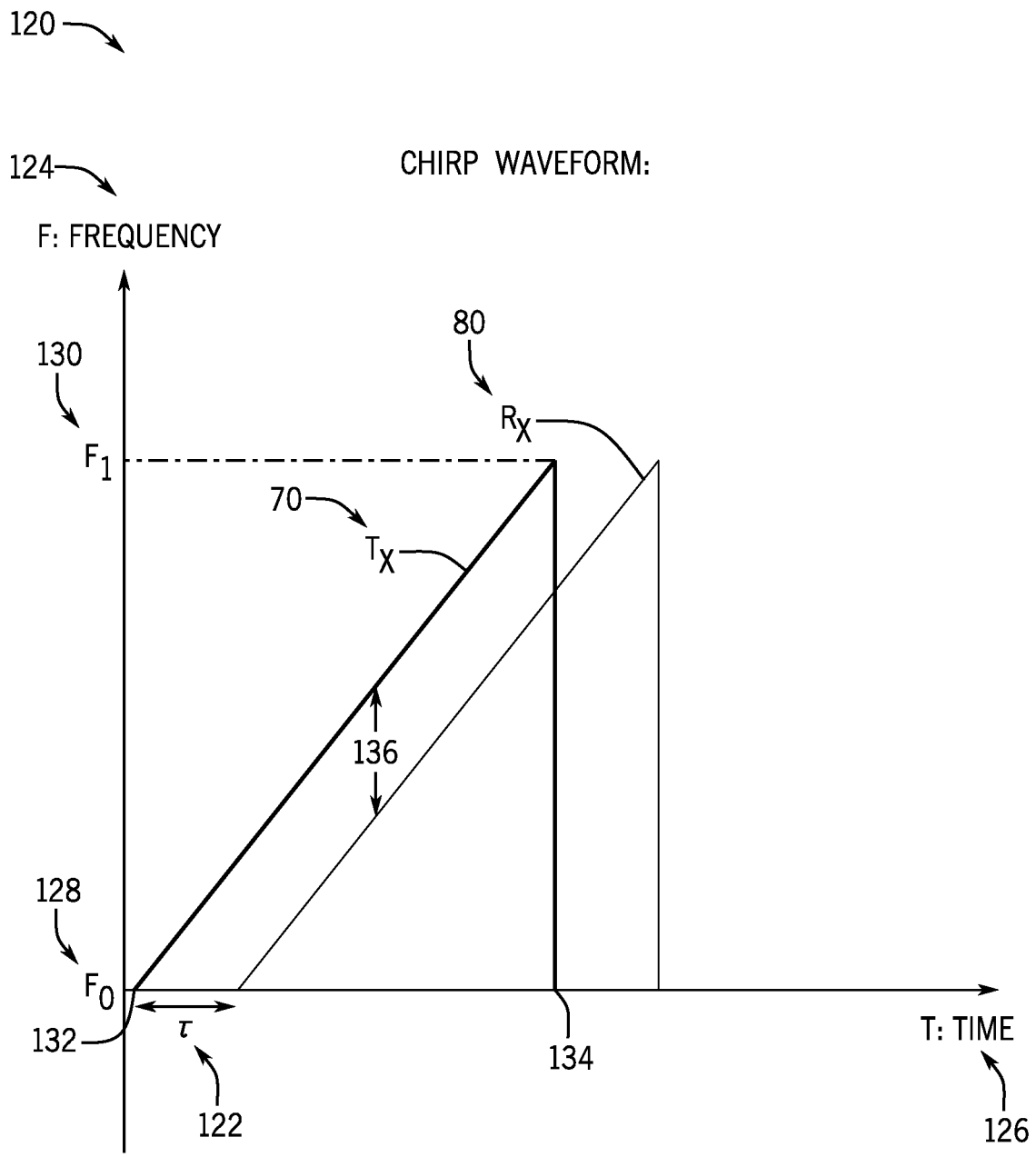
FIG. 6 is a graph of a roundtrip time delay between a transmitted chirp signal and a received chirp signal, according to embodiments of the present disclosure.

FIG. 6 depicts a graph 120 illustrating a roundtrip time delay ($\tau$) 122 between the transmitted signal 70 and the received signal 80. The graph 120 may include a frequency axis 124 and a time axis 126. Moreover, in the depicted embodiment, the transmitted signal 70 and the received signal 80 may each include a chirp signal. However, it should be appreciated that in other embodiments, the transmitted signal 70 and the received signal 80 may have a constant oscillation frequency. In any case, the depicted chirp signals (the transmitted signal 70 and the received signal 80) may have an increasing oscillation frequency over time.

For example, the transmitted signal 70 may oscillate at a low frequency ($f_0$) 128 at a first time (or initial time) 132 and a high frequency ($f_1$) 130 at a second time 134. With that in mind, the transmitted signal 70 and the received signal 80 may be time-shifted based on the roundtrip time delay ($\tau$) 122. For example, as discussed above with respect to FIG. 5, the roundtrip time delay ($\tau$) 122 may be based on the distance ($R_0$) 108 of the point target 100 from the radar system 30. Accordingly, based on the roundtrip time delay ($\tau$) 122 and the increasing frequency of the chirp signals, the transmitted signal 70 may be separated from the received signal 80 by a frequency difference $f_B(\tau)$ 136 or beat frequency at each point in time.

The processor 12 may determine the frequency difference $f_B(\tau)$ 136, which may be constant or near constant over time based on the constant or near constant roundtrip time delay ($\tau$) 122. For example, the processor 12 may use Equation 2 below for determining the frequency difference $f_B(\tau)$ 136, where k may be a chirp signal slope of the oscillation frequency of the transmitted signal 70.

$$f_B(\tau) = k\frac{2R_0}{c} \quad \text{(Equation 2)}$$

Moreover, the processor 12 may determine a second distance $R(\tau)$ to the point target 100 based on the distance ($R_0$) 108 and the frequency difference $f_B(\tau)$ 136. Based on accounting for the frequency difference $f_B(\tau)$ 136 using information related to the differential phases and/or frequency modulations caused by reflection from the point target 100, the second distance $R(\tau)$ may include the fine grain motions and/or vibrations of a live object (e.g., human body). In some cases, the processor 12 may determine the second distance $R(\tau)$ using the Equation 3 below. In the Equation 3 below, $x(t, \tau)$ may refer to the combined signal 110, output from the RF mixer 84. Moreover, wavelength $\lambda$ may be based on the low frequency ($f_0$) 128, the high frequency ($f_1$) 130, or another frequency between $f_0$ and $f_1$. Furthermore, time t may be a time associated with the wavelength $\lambda$.

$$x(t, \tau) = e^{-j\frac{4\pi}{\lambda}R(\tau)} \cdot e^{-j2\pi f_B(\tau)t} \quad \text{(Equation 3)}$$

Moreover, in some embodiments, the processor 12 may use Equation 4 below to extract vibrations $\Delta R(\tau)$ indicative of the fine grain motions and/or vibrations of a live object (e.g., human body). The processor 12 may determine the vibrations $\Delta R(\tau)$ based on the second distance $R(\tau)$ and the distance ($R_0$) 108 of the point target 100. Subsequently, in some cases, the processor 12 may use Equation 5 below to determine any rotations (e.g., changes) in the phase of the received signal 80 based on the transmitted signal 70.

$$R(\tau) = R_0 + \Delta R(\tau) \quad \text{(Equation 4)}$$

$$\Delta\varphi = \frac{4\pi}{\lambda} \cdot \Delta R(\tau) \quad \text{(Equation 5)}$$

The processor 12 may use the differential phase $\Delta\varphi$ across consecutive time epochs (e.g., time segments) to determine biometric information associated with the point target 100. Moreover, the processor 12 may also perform statistical analysis based on determining multiple differential phases $\Delta\varphi$ associated with multiple transmitted signals 70 transmitted across different time epochs for determining multiple vibrations $\Delta R(\tau)$ of the point target 100, as will be appreciated.

For example, the processor 12 may filter multiple received signals using one or multiple spatial gating setting. In some cases, the spatial gating setting may include a spatial dimension range, a range of distance from the electronic device 10, an angular resolution range, and/or other parameters or combination of parameters associated with a live object (e.g., the human body). For example, the processor 12 may fuse multiple differential phases $\Delta\varphi$ or select one or more of the differential phases $\Delta\varphi$ to determine the vibrations $\Delta R(\tau)$ of the point target 100, as will be appreciated. In such embodiments, the processor 12 may provide more robust biometric information of the point target 100 (e.g., human body) based on performing the statistical analysis.

Figure 7:
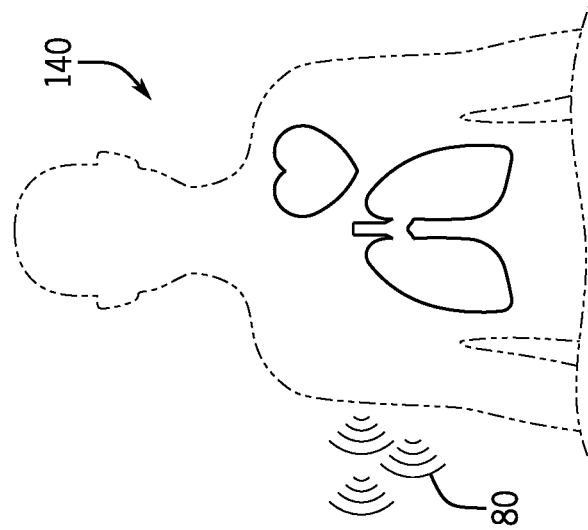
FIG. 7 is a diagram of the radar system of the electronic device of FIG. 1 transmitting signals to and receiving reflections from a human body, according to embodiments of the present disclosure.
Figure 7:
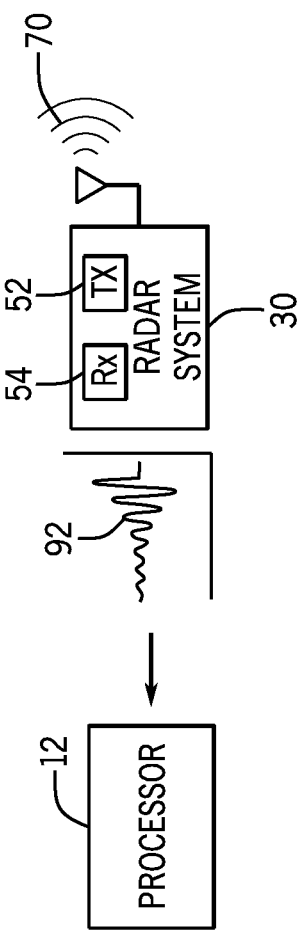

With the foregoing in mind, FIG. 7 depicts the point target 100 positioned on a human body 140. In the depicted embodiment, the transmitter 52 of the radar system 30 may send the transmitted signal 70 directed to the human body 140. Moreover, the receiver 54 may receive one or multiple subsets of the back-scattered signals (e.g., multiple target maps) reflected from the human body 140. For example, the human body 140 may include the point target 100 and other reflection points within one or multiple spatial regions of the human body 140. That said, in some embodiments, the human body 140 may be replaced by any other live or animate object.

The point target 100 may also have different shapes or sizes based on a field of view of the radar system 30. For example, in the depicted embodiment, the field of view of the radar system 30 may include a portion of the human body 140. In some cases, the receiver 54 may distinguish between different spatial regions of the human body 140 within the field of view of the radar system 30, for example, based on a distance, an angle, doppler information, and/or other parameter or combination of information associated with the multiple subsets of the back-scattered signals on the human body 140. However, in other embodiments, the field of view of the radar system 30 may include the entire human body 140. In yet other embodiments, the field of view of the radar system 30 may include an area associated with multiple live objects including, for example, the human body 140.

In any case, as described above, the receiver 54 may process (e.g., combine, filter, demodulate, and/or convert to digital data) the received signal 80, and output the processed signal 92 to the processor 12. Subsequently, the processor 12 may extract biometric information from the incoming signal 92. For example, as mentioned above, the processor 12 may determine differential phases $\Delta\varphi$ associated with transmitted signals 70 for determining vibrations $\Delta R(\tau)$ of the human body 140. Moreover, the processor 12 may determine differential phases $\Delta\varphi$ associated with multiple subsets of the back-scattered signals associated with different distances, angles, doppler information, and/or other parameters for determining vibrations $\Delta R(\tau)$ of the human body 140.

In some cases, the processor 12 may also determine differential phases $\Delta\varphi$ associated with multiple live objects. As mentioned above, subsequently, the processor 12 may determine the biometric information including respiratory and/or cardiovascular information of the human body 140 based on the one or multiple subsets of the back-scattered signals. The respiratory and/or cardiovascular information of the human body 140 may include a rate of breathing, a rate of heartbeat, coughing, sneezing, tremors, seizures, and/or other movements or vibrations of the human body, or any combination of the above.

Figure 8:
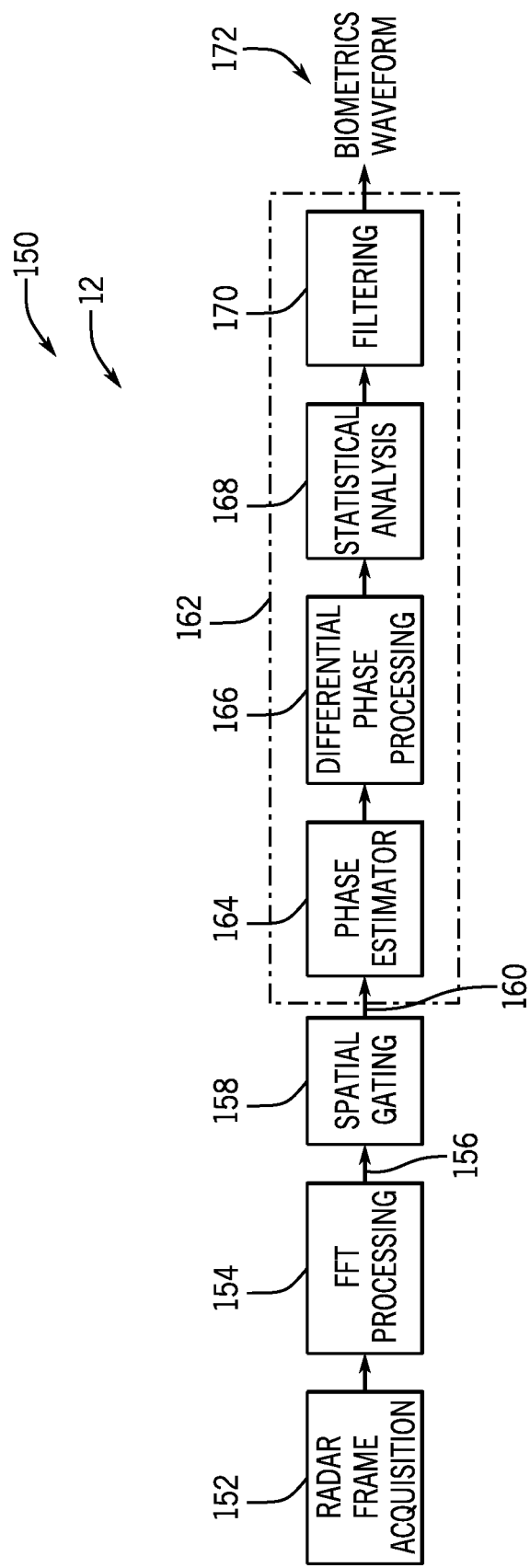
FIG. 8 is a block diagram of processing stages for determining motions and/or vibrations of a live object using a statistical biometric processor, according to embodiments of the present disclosure.

Referring now to FIG. 8, processing stages 150 for determining the fine grain motions and/or vibrations of a live object (e.g., the human body 140) using a differential phase statistics technique are depicted. For example, the processor 12 may perform the processing stages 150 to provide a biometric waveform indicative of biometric information of the human body 140. At radar frame acquisition block 152, the processor 12 may receive multiple incoming signals 92 across subsequent time epochs. For example, the multiple incoming signals 92 across subsequent time epochs may include different radar pulses, chirp signals, or frames of signals. Moreover, as mentioned above, the radar system 30 depicted in FIGS. 1, 2, 5, and 7 may provide the incoming signals 92 to the processor 12. Moreover, the incoming signals 92 may include the received signals 80 combined with an instance of a corresponding transmitted signal 70.

At Fast Fourier Transform (FFT) processing block 154, the processor 12 may process the incoming signals 92 that are received in the time domain to generate frequency domain signals. For example, at the FFT processing block 154, the processor 12 may perform fast-time Fourier transform, slow-time Fourier transform, or other processing technique, to generate frequency domain incoming signals 92. In additional or alternative cases, the FFT processing block 154 may perform Discrete-Time Fourier-Transform (DTFT). Accordingly, the FFT processing block 154 may output a full target map 156 comprising the frequency domain incoming signals 92. The full target map 156 may include the frequency domain incoming signals 92 with corresponding distance, angle, doppler information, and/or any other parameter or combination of information associated with a location of one or more point targets. For example, the one or more point targets may include the point target 100 and/or other point targets positioned on the human body 140 and/or different live objects, as will be appreciated. Subsequently, using such information provided with the incoming signals 92, the processor 12 may select a subset of (or a portion of) the full target map 156 at spatial gating block 158. As such, the spatial gating block 158 may output a gated target map 160 that is or includes the subset of the full target map 156.

In some cases, the spatial gating block 158 may select the subset of the incoming signals 92 for further processing based on a distance range, an angular range, location information, dimension information, any other viable parameter or combination of parameters associated with an observed live object (e.g., the human body 140). Accordingly, the gated target map 160 may include a subset of (or a portion of) the frequency domain incoming signals 92 received with the full target map 156.

Subsequently, a biometric processor block 162 may receive the gated target map 160. The biometric processor block 162 may include a phase estimator block 164, a differential phase processing block 166, a statistical analysis block 168, and a filtering block 170 for processing the gated target map 160, as discussed in more details below. Subsequently, the biometric processor block 162 may output biometrics waveform 172 indicative of biometric information associated with the live target.

At the phase estimator block 164, the processor 12 may determine a phase $\varphi$ of the subset of the frequency domain incoming signals 92 associated with the gated target map 160. Moreover, the phase estimator block 164 may determine a coherent or non-coherent phase values $\varphi$. In some cases, the phase estimator block 164 may include storage and/or memory (e.g., the memory 14, the storage 16, or both) to store multiple phase values $\varphi$ across different time epochs.

In any case, the phase estimator block 164 may provide the determined phase values $\varphi$ to the differential phase processing block 166 for determining the differential phases $\Delta\varphi$ of the subset of the frequency domain incoming signals 92 across subsequent time epochs. In some cases, the processor 12 may determine the differential phases $\Delta\varphi$ based on the Equations 1-5 described above. In other cases, the processor 12 may use other techniques or equations for determining the differential phases $\Delta\varphi$. Accordingly, the phase estimator block 164 may provide the differential phases $\Delta\varphi$ to the statistical analysis block 168.

That said, in some cases, the phase estimator block 164 may also use the phase values $\varphi$ of previous time epochs (e.g., looking back in time), stored and provided by the phase estimator block 164, to determine the differential phases $\Delta\varphi$. For example, the processor 12 may determine the biometric information based on determining differential phases $\Delta\varphi$ between consecutive time epochs or previous consecutive time epochs (e.g., looking back in time). Moreover, in some cases, the processor 12 may use phase values $\varphi$ of consecutive time epochs with different differential times between such time epochs. For example, the processor 12 may use shorter or longer time epochs based on the available phase values $\varphi$ provided by the phase estimator block 164.

In any case, the processor 12 may subsequently determine a statistical analysis of the differential phases $\Delta\varphi$ across time to determine the vibrations of the observed live object (e.g., the human body 140) at the statistical analysis block 168. In some cases, the processor 12 may determine a mode, a mean, a variance, an ordered statistics value, and/or other statistics of incoming signals 92 at the statistical analysis block 168. For example, the processor 12 may receive the consecutive incoming signals 92 across consecutive time epochs, and determine a statistical analysis of the consecutive incoming signals 92.

Moreover, at the statistical analysis block 168, the processor 12 may exclude outlier data based on the statistical analysis of the differential phases $\Delta\varphi$ to determine a set of normality data. For example, a phase $\varphi$ of some of the consecutive incoming signals 92 may be erroneous. In some cases, the processor 12 may exclude outlier data based on determining that phase values φ and/or differential phases exceed a threshold phase value or a threshold phase rotation value. Moreover, the processor 12 may determine the threshold phase rotation value based on the statistical analysis of the phase values φ and/or differential phases. Accordingly, the processor 12 may determine the normality set of differential phases Δφ by excluding the outlier data.

In some cases, movement and/or vibrations of the human body 140 may cause a phase wrapping effect, various destructive or constructive interferences such as multipath fading and/or clutter/interference phase reference translation, and/or other errors. As such, such behaviors may result in erroneous phase values φ and/or differential phases Δφ. Moreover, such erroneous differential phases Δφ may occur infrequently. Accordingly, the processor 12 may exclude incoming signals 92 corresponding to such outlier differential phases Δφ based on the statistical analysis of the differential phases Δφ.

At the filtering block 170, the processor 12 may integrate the differential phases Δφ to determine a real-valued time-series waveform. The processor 12 may integrate the remaining differential phases Δφ (e.g., the normality set of differential phases) based on excluding the outlier differential phases Δφ at the statistical analysis block 168 described above. Moreover, the processor 12 may determine the real-valued time-series waveform to provide a relative distance of the live object from the radar system 30 at each point in time. For example, the processor 12 may use the remaining differential phases Δφ (e.g., the normality set of differential phases) to indicate the fine grain motions and/or vibrations of the live object in the real-valued time-series waveform.

Furthermore, in some cases, the processor 12 may perform spectral selectivity, filter noises, and/or remove possible biases in the real-valued time-series waveform at the filtering block 170. Subsequently, the biometric processor block 162 may output the biometrics waveform 172 indicative of the biometric information associated with the live target. In some embodiments, the biometrics waveform 172 may include a breathing waveform, a heartbeat waveform, a superposition of the breathing waveform and the heartbeat waveform, or other biometric information of the live object.

Figure 9:
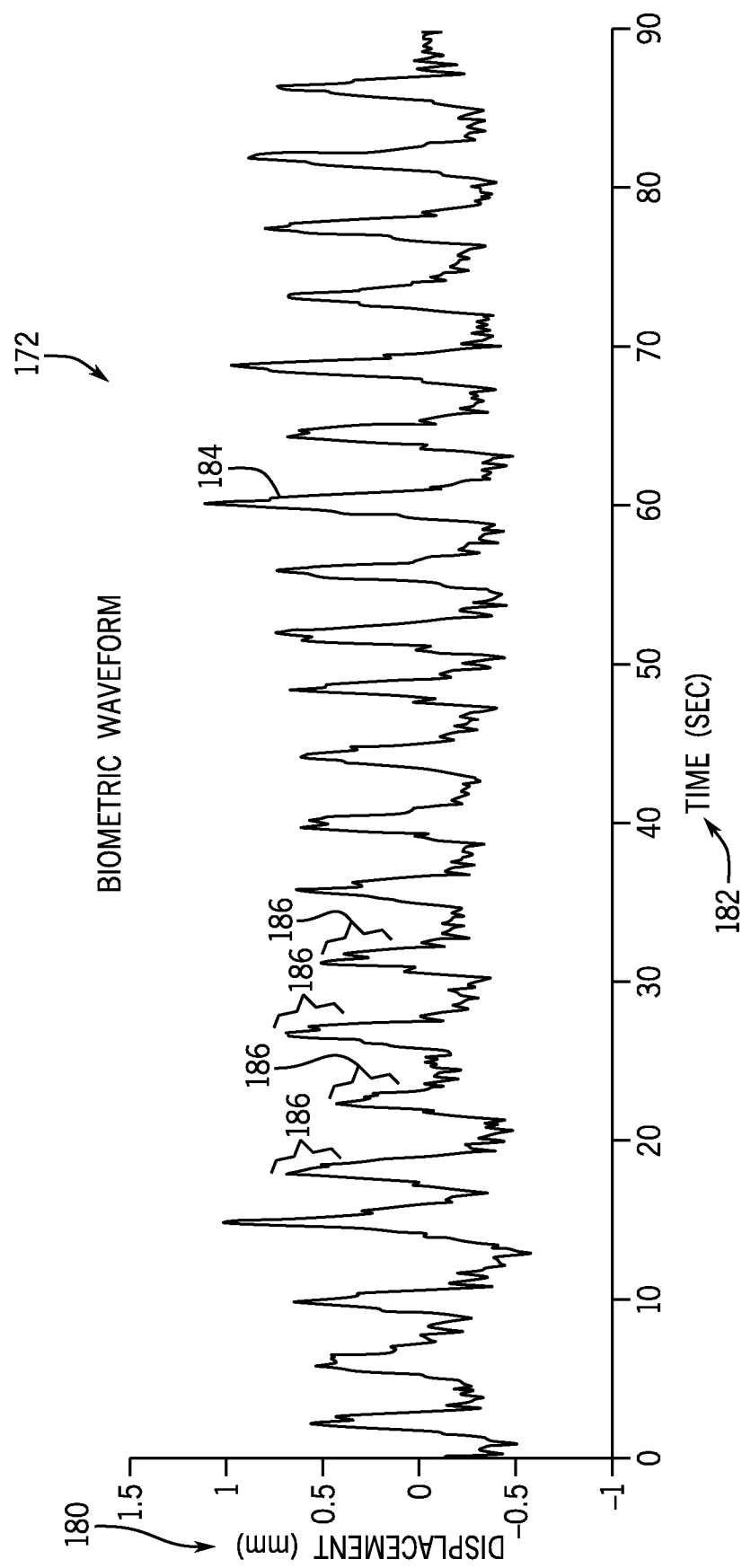
FIG. 9 is an example of a biometrics waveform output from the processing stages of FIG. 8, according to embodiments of the present disclosure.

FIG. 9 depicts an example of the biometrics waveform 172 discussed above. The biometrics waveform 172 may be shown by displacement 180 in millimeters over time 182 in seconds. That said, in other embodiments different units of measurements may be used. In the depicted embodiment, the biometrics waveform 172 may include a superposition of a breathing waveform 184 and a heartbeat waveform 186. The processor 12 may perform processing (e.g., FFT processing) of the biometrics waveform 172 to extract the breathing waveform 184 and the heartbeat waveform 186. Moreover, in other cases, the biometrics waveform 172 may include other biometric information or superposition/combination of other biometric information.

In yet other cases, the processor 12 may receive multiple biometric waveforms including the biometrics waveform 172. In some embodiments, the processor 12 may fuse all or a number of the multiple biometric waveforms to determine yet more robust biometric information. In alternative or additional embodiments, the processor 12 may select a number of the multiple biometric waveforms having the most accurate biometric information. Examples of such embodiments are discussed in more details below.

Figure 10:
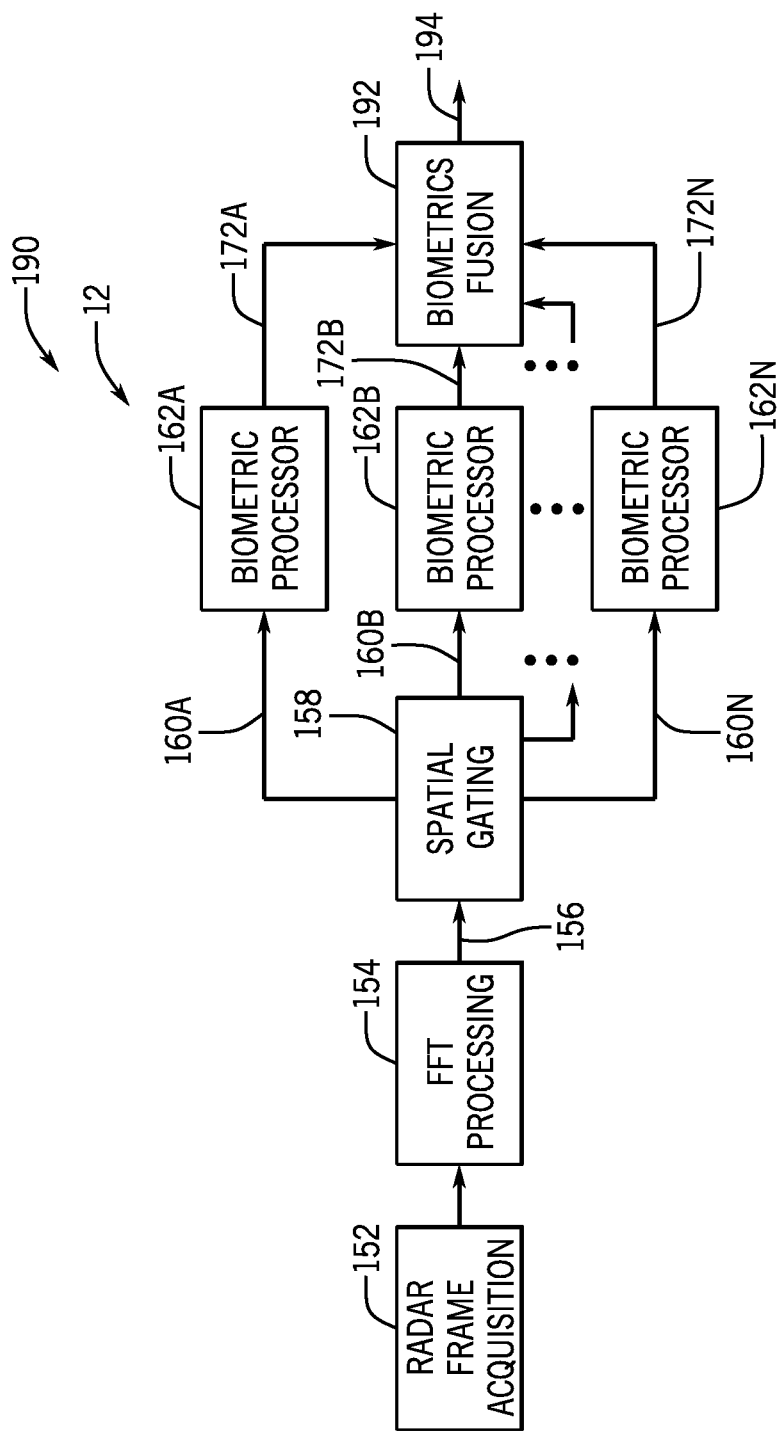
FIG. 10 is a block diagram of processing stages for determining motions and/or vibrations of a live object using multiple statistical biometric processors, according to an embodiments of the present disclosure.

FIG. 10 depicts an alternative or additional embodiment of the processor 12 using the biometric processor block 162 for determining statistical analysis of the received signals 80. FIG. 10 includes processing stages 190 for determining the fine grain motions and/or vibrations of a live object (e.g., the human body 140) using multiple biometric processor blocks 162A-162N. For example, the processor 12 may provide multiple biometric waveforms 172A-172N each indicative of biometric information of the human body 140. With the foregoing in mind, based on operations associated with the radar frame acquisition block 152 and the FFT processing block 154, the processor 12 may provide the full target map 156 to the spatial gating block 158.

At the spatial gating block 158, the processor 12 may provide multiple (e.g., 2 or more, 3 or more, 10 or more, and so on) gated target maps 160A-160N each including a subset of the full target map 156 that maps the incoming signals 92. In some cases, the spatial gating block 158 may select each subset of the incoming signals 92 for further processing based on a different distance range, angular range, location information, dimension information, and/or any other viable parameter or combination of parameters. Moreover, such parameters may be associated with one or multiple observed live objects (e.g., the human body 140).

The gated target map 160A may include a first subset of (or a portion of) the frequency domain incoming signals 92 received with the full target map 156. For example, the first subset may include frequency domain incoming signals 92 that are within a first distance range, angular range, or both. Moreover, the gated target map 160B may include a second subset of the frequency domain incoming signals 92 received with the full target map 156. For example, the second subset may include frequency domain incoming signals 92 that are within a second distance range, angular range, or both. That said, each of the gated target maps 160A-160N may be associated with similar or different parameters.

In some embodiments, the gated target maps 160A-160N may be associated with different parts of one live object. For example, breathing rate and heartbeat rate of the human body 140 may be constant or near constant at different parts of the body. Accordingly, the gated target maps 160A-160N may be directed to different parts of the human body 140 for a more robust measurement of the breathing rate and heartbeat rate of the human body 140. In alternative or additional embodiments, the gated target maps 160A-160N may be associated with different live objects. Accordingly, the gated target maps 160A-160N may be directed to different live objects.

Figure 11:
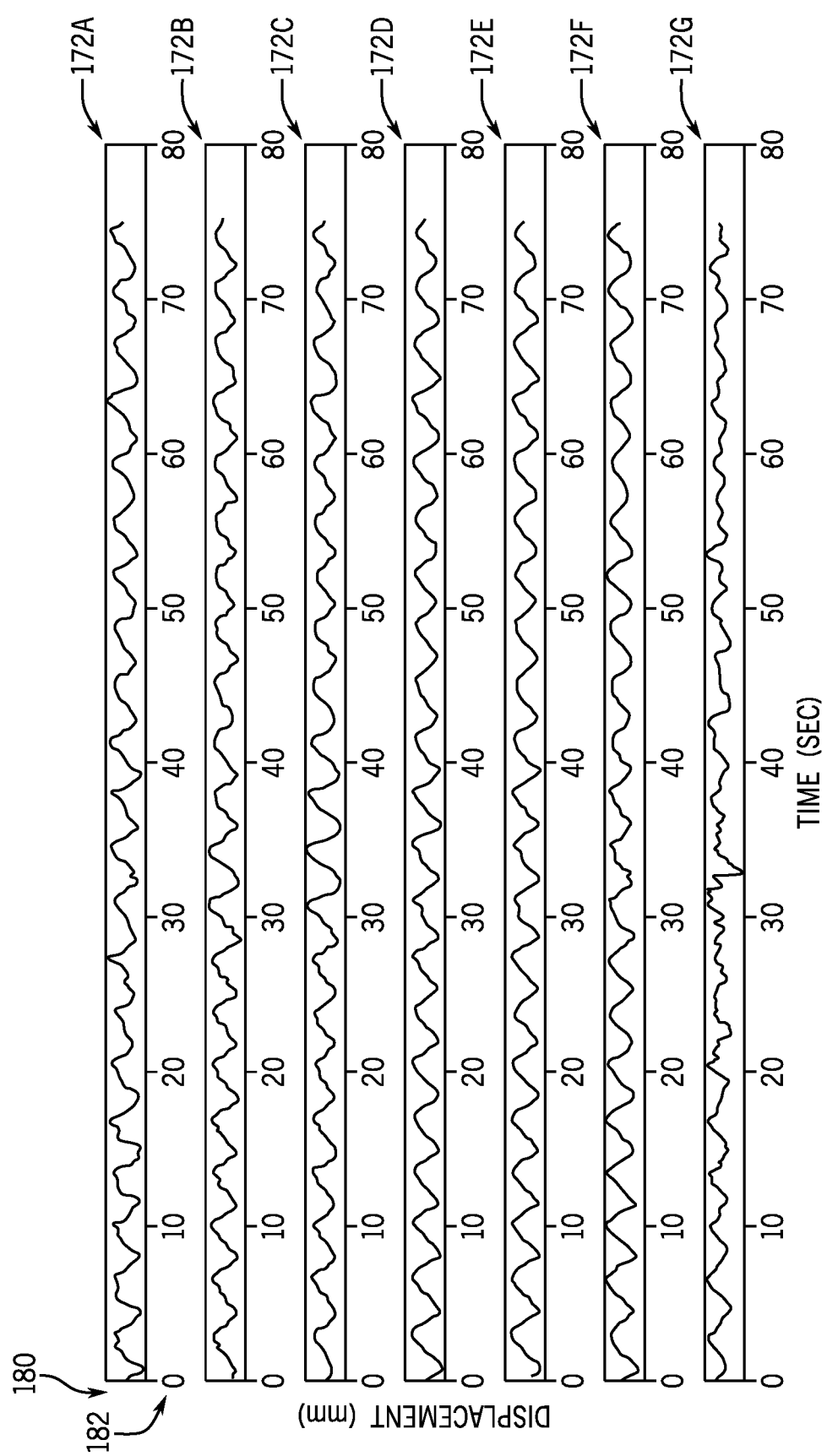
FIG. 11 is an example of multiple biometric waveforms output from the processing stages of FIG. 10, according to embodiments of the present disclosure.

In any case, biometric processor blocks 162A-162N may receive the gated target maps 160A-160N. Similar to the embodiment of FIG. 8, the biometric processor blocks 162A-162N may each include a phase estimator block 164, a differential phase processing block 166, a statistical analysis block 168, and a filtering block 170 for processing the gated target map 160. Subsequently, the biometric processor blocks 162A-162N may output biometric waveforms 172A-172N. For example, one or more of the biometric processor blocks 162A-162N may output the biometric waveforms 172A-172N based on determining a respective normality set of differential phases by excluding outlier data. As discussed above, in alternative or different embodiments, the biometric waveforms 172A-172N may be indicative of biometric information associated with one or multiple live targets. An example embodiment of the biometric waveforms 172A-172N are depicted in FIG. 11 and discussed below.

In some embodiment, a biometric fusion block 192 may receive the biometric waveforms 172A-172N. At the biometric fusion block 192, the processor 12 may fuse (e.g., combine) the biometric waveforms 172A-172N (e.g., biometric time-series data) to determine a fused biometric waveform. In some cases, the biometric fusion block 192 may coherently and/or non-coherently combine the biometric waveforms 172A-172N. For example, the biometric fusion block 192 may combine the biometric waveforms 172A-172N to improve a signal to noise ratio of the biometric waveforms and/or provide diversity gain to the biometric waveforms.

In alternative or additional cases, the biometric fusion block 192 may determine a mean, median, average, or some other statistical value of the biometric waveforms 172A-172N. In yet alternative or additional cases, the biometric fusion block 192 may select one or more of the biometric waveforms 172A-172N having more robust estimation of the biometric information and/or determine a statistical value of the biometric waveforms 172A-172N. In some embodiments, the biometric fusion block 192 may determine a first order harmonic waveform of the biometric time-series data, one or multiple higher order harmonic waveforms, or a combination of two or more harmonic waveforms with different orders to determine a breath rate, a heart rate, or both. In any case, the processor 12 may provide a fused biometric waveform 194.

That said, in some cases, the processor 12 may also bypass the biometric fusion block 192. In some cases, the processor 12 may select a number of the biometric waveforms 172A-172N having more robust estimation of the biometric information. For example, the processor 12 may select the biometric waveforms 172A-172N with lower numbers of outlier data (e.g., outlier phase values φ and/or differential phases Δφ). Alternatively, the processor 12 may select a number of the biometric waveforms 172A-172N having more robust estimation of the biometric information in parallel with using the biometric fusion block 192 to provide the fused biometric waveform 194. That said, the processor 12 may perform different operations associated with each of the biometric waveforms 172A-172N in parallel, consecutively, or in any viable order.

FIG. 11 depicts an example of the biometric waveforms 172A-172G output from biometric processor blocks 162A-162G of FIG. 10 discussed above. Similar to the embodiment of FIG. 9, the biometric waveforms 172A-172G may be shown by displacement 180 in millimeters over time 182 in seconds. That said, in other embodiments different units of measurements may be used. For example, each of the biometric waveforms 172A-172G may include a breathing waveform, a heartbeat waveform, or a superposition waveform comprising both.

In some embodiments, the processor 12, for example at the biometric fusion block 192 described above, may fuse all or a number of the multiple biometric waveforms to determine yet more robust biometric information. In alternative or additional embodiments, the processor 12 may select a number of the multiple biometric waveforms having the most accurate biometric information. Moreover, the processor 12 may perform processing (e.g., FFT processing) of the biometric waveforms 172A-172G to extract the breathing waveform, the heartbeat waveform, and/or other biometric information.

Figure 12:
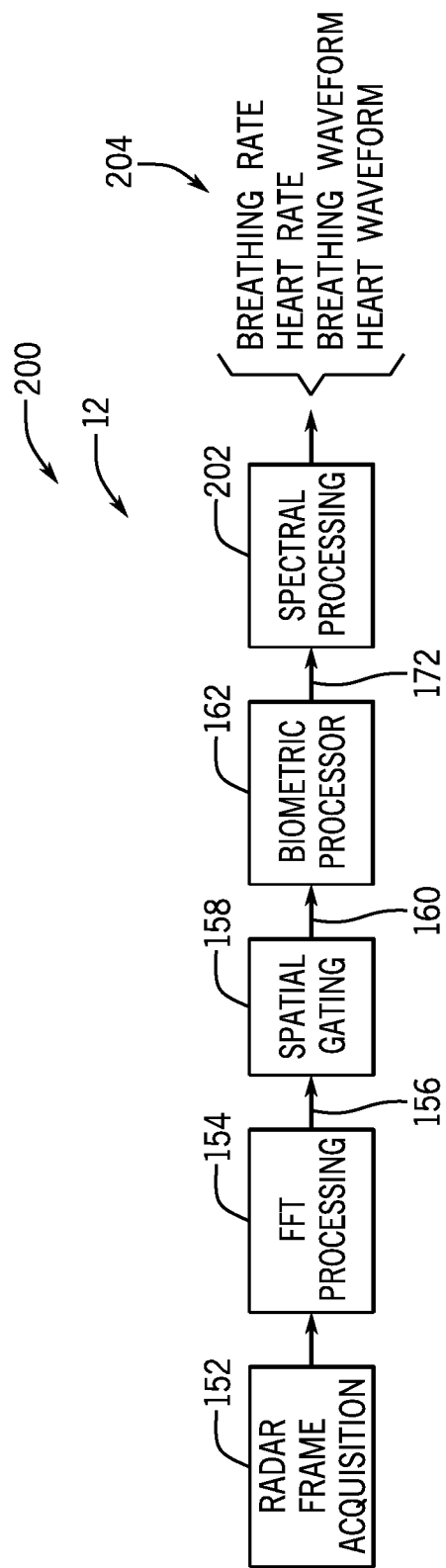
FIG. 12 is a block diagram of processing stages for determining motions and/or vibrations of a live object using a spectral processing technique, according to embodiments of the present disclosure.

FIG. 12 depicts an alternative or additional embodiment of the processor 12 using the biometric processor block 162 for determining statistical analysis of the received signals 80. FIG. 12 includes processing stages 200 for determining the fine grain motions and/or vibrations of a live object (e.g., the human body 140) based on using a spectral processing block 202. The spectral processing block 202 may receive the biometric waveform 172 and extract biometric information of the live object.

In some cases, the spectral processing block 202 may determine a time-frequency spectrogram of the biometric waveform 172. For example, the spectral processing block 202 may use a spectral estimation processing, Bayesian processing, or any other viable processing function for determining biometric information 204. The spectral processing block 202 may provide a time-frequency estimation of the biometric waveform 172. For example, in some embodiments, the spectral processing block 202 may provide a first order harmonic waveform, a second order harmonic waveform, other order of the time-frequency estimation of the biometric waveform 172, or a combination of such waveforms. As such, the spectral processing block 202 may determine the time-frequency spectrogram of the biometric waveform 172.

Although in the depicted embodiment, the biometric information 204 may include a breathing rate, a heart rate, a breathing waveform, and a heart waveform, the processor 12 may determine alternative or additional biometric information based on determining the time-frequency spectrogram of the biometric waveform 172. Moreover, in alternative embodiments, multiple biometric processor blocks 162A-162N may provide multiple biometric waveforms 172A-172N to the spectral processing block 202. In some cases, the processor 12 may perform operations of the biometric fusion block 192 described above, in parallel or consecutively with the operations of the spectral processing block 202. For example, the spectral processing block 202 may include the biometric fusion block 192.

Figure 13:
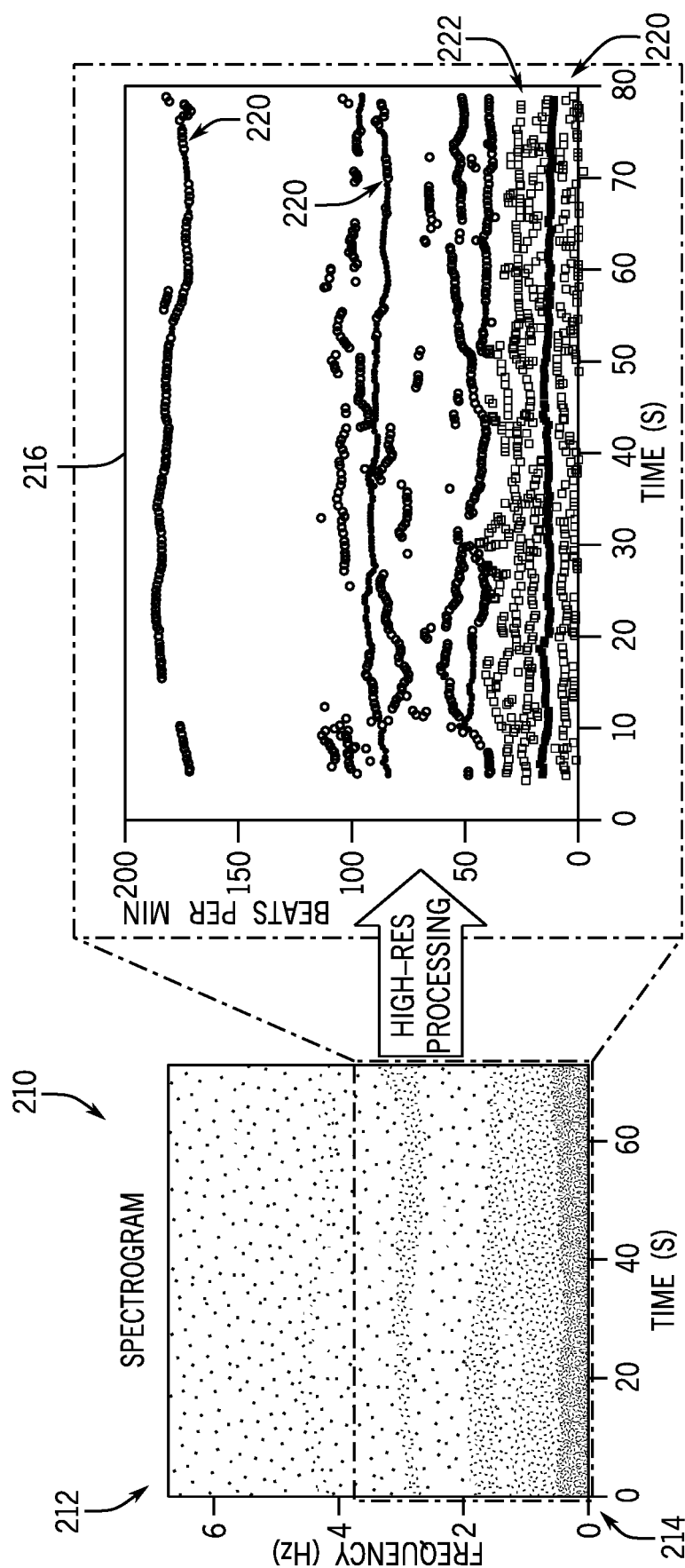
FIG. 13 depicts a spectrogram of biometric waveform output by the spectral processing technique of FIG. 12, according to embodiments of the present disclosure.

With the foregoing in mind, FIG. 13 depicts a spectrogram 210 of the biometric waveform 172 provided by the spectral processing block 202 discussed above. The spectrogram 210 may illustrate the biometric waveform 172 over a frequency range 212 and a time 214. That said, the processor 12 may receive and process the spectrogram 210 to determine a time representation 216 of the biometric information 204. In the depicted example, the time representation 216 may include a heart rate 220 and a breathing rate 222 based on processing the spectrogram 210. Moreover, in the depicted example, multiple heart rates 220 and breathing rates 222 are determined based on processing different harmonic orders of the spectrogram 210. That said, the processor 12 may determine the desired or correct heart rate 220 and breathing rate 222 from the multiple heart rates 220 and breathing rates 222.

Moreover, in specific cases, the spectrogram 210 and/or the time representation 216 of the biometric information 204 may be used for identifying a live object and/or distinguishing the live object from other objects, including other live objects. For example, different human bodies may be associated with different and unique first, second, third, or Nth order harmonic waveforms (e.g., time representations and/or time-frequency estimations). Accordingly, the processor 12 or other processing circuitry may use the spectrogram 210 and/or the time representation 216 for identifying and/or distinguishing a live object, for example, among multiple live objects.

As described above, one aspect of the present technology is the gathering and use of data available from specific and legitimate sources to improve the delivery to users of invitational content or any other content that may be of interest to them. The present disclosure contemplates that in some instances, this gathered data (e.g., biometric information) may include personal information data that uniquely identifies or can be used to identify a specific person. Such personal information data can include demographic data, location-based data, online identifiers, telephone numbers, email addresses, home addresses, data or records relating to a user's health or level of fitness (e.g., vital signs measurements, medication information, exercise information), date of birth, or any other personal information.

The present disclosure recognizes that the use of such personal information data, in the present technology, can be used to the benefit of users. For example, the personal information data can be used to deliver targeted content that may be of greater interest to the user in accordance with their preferences. Accordingly, use of such personal information data enables users to have greater control of the delivered content. Further, other uses for personal information data that benefit the user are also contemplated by the present disclosure. For instance, health and fitness data may be used, in accordance with the user's preferences to provide insights into their general wellness, or may be used as positive feedback to individuals using technology to pursue wellness goals.

The present disclosure contemplates that those entities responsible for the collection, analysis, disclosure, transfer, storage, or other use of such personal information data will comply with well-established privacy policies and/or privacy practices. In particular, such entities would be expected to implement and consistently apply privacy practices that are generally recognized as meeting or exceeding industry or governmental requirements for maintaining the privacy of users. Such information regarding the use of personal data should be prominent and easily accessible by users, and should be updated as the collection and/or use of data changes. Personal information from users should be collected for legitimate uses only. Further, such collection/sharing should occur only after receiving the consent of the users or other legitimate basis specified in applicable law.

Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations that may serve to impose a higher standard. For instance, in the US, collection of or access to certain health data may be governed by federal and/or state laws, such as the Health Insurance Portability and Accountability Act (HIPAA); whereas health data in other countries may be subject to other regulations and policies and should be handled accordingly.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, such as in the case of advertisement delivery services, the present technology can be configured to allow users to select to "opt in" or "opt out" of participation in the collection of personal information data during registration for services or anytime thereafter. In another example, users can select not to provide mood-associated data for targeted content delivery services. In yet another example, users can select to limit the length of time mood-associated data is maintained or entirely block the development of a baseline mood profile. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing identifiers, controlling the amount or specificity of data stored (e.g., collecting location data at city level rather than at an address level), controlling how data is stored (e.g., aggregating data across users), and/or other methods such as differential privacy.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users based on aggregated non-personal information data or a bare minimum amount of personal information, such as the content being handled only on the user's device or other non-personal information available to the content delivery services.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ," it is intended that such elements are to be interpreted under 35 U.S.C. 112(f). However, for any claims containing elements designated in any other manner, it is intended that such elements are not to be interpreted under 35 U.S.C. 112(f).

It is well understood that the use of personally identifiable information should follow privacy policies and practices that are generally recognized as meeting or exceeding industry or governmental requirements for maintaining the privacy of users. In particular, personally identifiable information data should be managed and handled so as to minimize risks of unintentional or unauthorized access or use, and the nature of authorized use should be clearly indicated to users.

The invention claimed is:

1. An electronic device comprising:
a transmitter configured to transmit a plurality of transmitted signals toward a live target;

a receiver configured to receive a plurality of reflections of the plurality of transmitted signals reflected from the live target; and one or more processors configured to
receive the plurality of transmitted signals from the transmitter,
receive the plurality of the reflections from the receiver,
determine a first plurality of differential phases based on a first subplurality of the plurality of reflections and a first subplurality of the plurality of transmitted signals, and
generate first biometric time-series data based on the first plurality of differential phases.

2. The electronic device of claim 1, wherein the one or more processors are configured to determine a normality set of differential phases by excluding one or more outlier differential phases of the first plurality of differential phases.

3. The electronic device of claim 2, wherein the one or more processors are configured to generate the first biometric time-series data based on the normality set of differential phases.

4. The electronic device of claim 2, wherein the one or more processors are configured to determine the one or more outlier differential phases based on determining a mean value, an average value, a mode value, a variance value, an ordered statistics value, or a combination thereof, of a number of differential phases of the first plurality of differential phases.

5. The electronic device of claim 2, wherein the one or more processors are configured to determine that a phase rotation of the one or more outlier differential phases is above a threshold to determine the one or more outlier differential phases.

6. The electronic device of claim 1, wherein the transmitter is configured to transmit the plurality of transmitted signals with increasing or decreasing frequency over a frequency range associated with a chirp signal.

7. The electronic device of claim 1, wherein the first subplurality of the plurality of reflections correspond to the first subplurality of the plurality of transmitted signals, wherein determining a differential phase of the first plurality of differential phases comprises combining a reflection of the first subplurality of the plurality of reflections with a corresponding signal of the first subplurality of the plurality of transmitted signals.

8. The electronic device of claim 1, wherein the one or more processors are configured to determine the first subplurality of the plurality of reflections based on a distance range, an azimuth range, an elevation range, a doppler dimension range, or a combination thereof of the plurality of the reflections.

9. The electronic device of claim 1, wherein the one or more processors are configured to:
determine a second plurality of differential phases based on a second subplurality of the plurality of reflections and a second subplurality of the plurality of transmitted signals, the second subplurality of the plurality of reflections being associated with a different distance range, azimuth range, elevation range, doppler dimension range, or a combination thereof compared to that of the first subplurality of the plurality of reflections,
generate second biometric time-series data based on the second plurality of differential phases,
fuse the first biometric time-series data and the second biometric time-series data to determine an output biometric time-series data associated with the live target, and
determine a breath rate, a heart rate, or both, associated with the live target by extracting one or more harmonic waveforms from the output biometric time-series data.

10. The electronic device of claim 1, wherein the one or more processors are configured to determine a breath rate, a heart rate, or both, associated with the live target by extracting one or more harmonic waveforms from the first biometric time-series data.

11. A method comprising:
receiving, by a processor, a plurality of reflections back-scattered from a live target;
determining, by the processor, a first target map comprising a first subplurality of the plurality of reflections associated with a first distance range, azimuth range, elevation range, doppler dimensions range, or any combination thereof of the plurality of reflections;
determining, by the processor, a first biometric time-series data associated with the live target based on a number of the plurality of reflections of the first target map;
determining, by the processor, a second target map comprising a second subplurality of the plurality of reflections associated with a second distance range, azimuth range, elevation range, doppler dimensions range, or any combination thereof of the plurality of reflections;
determining, by the processor, a second biometric time-series data associated with the live target based on a number of the reflections of the second target map; and
fusing, by the processor, the first biometric time-series data and the second biometric time-series data to determine an output biometric time-series data associated with the live target.

12. The method of claim 11, wherein the first biometric time-series data is indicative of breathing rate information, heart rate information, or both of the live target.

13. The method of claim 11, comprising:
receiving, by the processor, a plurality of transmitted signals transmitted to the live target, the plurality of transmitted signals corresponding to the plurality of reflections back-scattered from a live target;
determining, by the processor, a plurality of differential phases based on the first subplurality of the plurality of reflections and a first subplurality of the plurality of transmitted signals to determine the first target map; and
determining, by the processor, the first biometric time-series data based on the plurality of differential phases.

14. The method of claim 11, the method comprising excluding one or more outlier reflections of the first subplurality of the plurality of reflections prior to determining the first biometric time-series data.

15. The method of claim 11, wherein fusing the first biometric time-series data and the second biometric time-series data comprises determining that the first biometric time-series data or the second biometric time-series data comprises more robust estimation of biometric information associated with the live target.

16. The method of claim 11, wherein fusing the first biometric time-series data and the second biometric time-series data comprises determining a mean, a median, an average, or a combination thereof of the first biometric time-series data, the second biometric time-series data, or both.

17. The method of claim 11, wherein fusing the first biometric time-series data and the second biometric time-series data comprises determining breathing rate information, heart rate information, or both of the live target based on determining one or more harmonic waveforms of the first biometric time-series data, the second biometric time-series data, or both.

18. One or more tangible, non-transitory, computer-readable media comprising instructions that, when executed by one or more processors, cause the one or more processors to perform operations comprising:
   receiving, by the one or more processors, a plurality of reflections back-scattered from a live target;
   determining, by the one or more processors, a first target map comprising a first subplurality of the plurality of reflections associated with a first distance range, azimuth range, elevation range, doppler dimensions range, or any combination thereof of the plurality of reflections;
   determining, by the one or more processors, a first biometric time-series data associated with the live target based on a number of the reflections of the first target map;
   determining, by the one or more processors, a second target map comprising a second subplurality of the plurality of reflections associated with a second distance range, azimuth range, elevation range, doppler dimensions range, or any combination thereof of the plurality of reflections;
   determining, by the one or more processors, a second biometric time-series data associated with the live target based on a number of the reflections of the second target map; and
   provide, by the one or more processors, an output biometric time-series data associated with the live target based on the first biometric time-series data and the second biometric time-series data.

19. The one or more tangible, non-transitory, computer-readable media of claim 18, wherein the instructions, when executed by one or more processors, cause the one or more processors to perform operations comprising
   receiving, by the one or more processors, a plurality of transmitted signals transmitted to the live target, the plurality of transmitted signals corresponding to the plurality of reflections back-scattered from a live target;
   determining, by the one or more processors, a plurality of differential phases based on the first subplurality of the plurality of reflections and a first subplurality of the plurality of transmitted signals to determine the first target map; and
   determining, by the one or more processors, the first biometric time-series data based on the plurality of differential phases.

20. The one or more tangible, non-transitory, computer-readable media of claim 18, wherein the instructions, when executed by one or more processors, cause the one or more processors to perform operations comprising:
   determining, by the one or more processors, that the first biometric time-series data or the second biometric time-series data comprises more robust estimation of biometric information associated with the live target;
   determining, by the one or more processors, a mean, a median, an average, or a combination thereof of the first biometric time-series data, the second biometric time-series data, or both; or
   determining, by the one or more processors, breathing rate information, heart rate information, or both of the live target based on determining one or more harmonic waveforms of the first biometric time-series data, the second biometric time-series data, or both;
   to provide the output biometric time-series data.

* * * * *